(12) United States Patent
Imran

(10) Patent No.: US 10,238,868 B2
(45) Date of Patent: Mar. 26, 2019

(54) ACCESSORY APPLIANCE FOR USE WITH A PERSONAL DIGITAL ASSISTANT

(71) Applicant: Incube Labs, LLC, San Jose, CA (US)

(72) Inventor: Mir Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 1 day.

(21) Appl. No.: 15/410,712

(22) Filed: Jan. 19, 2017

(65) Prior Publication Data

US 2017/0203110 A1    Jul. 20, 2017

Related U.S. Application Data

(60) Provisional application No. 62/280,639, filed on Jan. 19, 2016.

(51) Int. Cl.
| | | |
|---|---|---|
| *A61N 1/00* | (2006.01) | |
| *A61N 1/36* | (2006.01) | |
| *A61N 1/05* | (2006.01) | |
| *A61N 1/372* | (2006.01) | |

(52) U.S. Cl.
CPC ....... *A61N 1/36007* (2013.01); *A61N 1/3605* (2013.01); *A61N 1/36139* (2013.01); *A61N 1/36171* (2013.01); *A61N 1/0556* (2013.01); *A61N 1/37247* (2013.01)

(58) Field of Classification Search
CPC .................................................. A61N 1/36007
USPC .......................................................... 607/41
See application file for complete search history.

(56) References Cited

U.S. PATENT DOCUMENTS

| | | |
|---|---|---|
| 2005/0055063 A1 | 3/2005 | Loeb et al. |
| 2005/0143783 A1 | 6/2005 | Boveja et al. |
| 2009/0138061 A1 | 5/2009 | Stephens et al. |
| 2013/0150940 A1 | 6/2013 | Wilson et al. |
| 2013/0241745 A1* | 9/2013 | Colvin, Jr. ........... A61B 5/0022 340/870.02 |
| 2013/0289647 A1 | 10/2013 | Bhadra et al. |
| 2014/0046398 A1 | 2/2014 | Sachs et al. |
| 2014/0249595 A1 | 9/2014 | Chancellor et al. |
| 2014/0253038 A1 | 9/2014 | Posa |
| 2017/0203100 A1 | 7/2017 | Imran |

FOREIGN PATENT DOCUMENTS

| | | |
|---|---|---|
| GB | 1577682 A | 10/1980 |
| WO | WO-2004000416 A1 | 12/2003 |

OTHER PUBLICATIONS

Co-pending U.S. Appl. No. 15/410,692, filed Jan. 19, 2017.
International search report with written opinion dated May 26, 2017 for PCT/US2017/014195.

* cited by examiner

*Primary Examiner* — Nadia A Mahmood

(74) *Attorney, Agent, or Firm* — Wilson Sonsini Goodrich and Rosati, P.C.; Joel M. Harris

(57) ABSTRACT

A system for controlling urination in a patient includes an implantable controller and an external device. The implantable controller includes circuitry and electrodes for stimulating the pudendal nerves in order to control urination. In addition, the implantable controller includes sensors for determining information on bladder fullness and for transmitting such information to an external device which is used for controlling the implanted controller. The external device will display when bladder filling exceeds a safe threshold level, allowing the patient and a caregiver to take appropriate steps to allow the patient to urinate.

10 Claims, 7 Drawing Sheets

FIG. 6A  Bipolar Cuff Electrodes

FIG. 7A  Tripolar Cuff Electrodes

ACCESSORY APPLIANCE FOR USE WITH A PERSONAL DIGITAL ASSISTANT

CROSS-REFERENCE TO RELATED APPLICATIONS

This application claims the benefit of priority to U.S. Provisional Application No. 62/280,639, filed Jan. 19, 2016, the entire content of which is incorporated herein by reference.

This application is also related to concurrently filed. U.S. patent application Ser. No. 15/410,692 which is incorporated by reference herein in its entirety for all purposes.

BACKGROUND OF THE INVENTION

Field of the Invention

Embodiments of the present invention relates to medical apparatus and methods. More particularly, embodiments of the present invent relate to systems and methods for allowing paralyzed and incontinent patients to selectively control urinary function with real-time information regarding bladder fullness.

Many disorders can result in loss of a patient's ability to voluntarily control bladder function. Most commonly, patients suffering from spinal cord injuries can lose not only the ability to voluntarily control urination, but also the ability to sense when the bladder is full. Such patients have usually had to rely on the chronic use of a Foley catheter which is placed through the urethra and has a distal tip residing in the bladder. Such Foley catheters present a constant risk of infection which is exacerbated by the frequent need to exchange for a new catheter. Moreover, Foley catheters usually drain into a bag which the patient must carry when away from home or a treatment facility. The need to carry the drain bag is a significant burden to many patients.

To at least partially overcome these problems, very promising new systems have been proposed which allow patients and their caregivers to selectively stimulate the pudenal nerves to control voiding of the bladder. Such systems can eliminate the need for Foley catheters and are described, for example, in US 2014/0249595, the full disclosure of which is incorporated herein by reference.

While a significant advance, such pudenal nerve stimulation systems do not alert the patient when the bladder is filled. Since many patients will have lost the ability to sense when the bladder is full, these patients may prolong periods between voiding, raising the pressure in the bladder above safe levels and risking injury to the kidneys.

For these reasons, it would be desirable to provide improved systems and methods for controlling urination via stimulation of the pudenal nerves. It would be particularly desirable if such systems and methods could provide feedback to a patient or caregiver regarding fullness of the patient's bladder. Even more particularly, it would be desirable if such feedback were provided in real time, frequently or continuously, and could provide alerts or alarms when certain pressure levels are approached, reached, or exceeded.

Description of the Background Art

US 2014/0249595, has been described above.

SUMMARY OF THE INVENTION

Embodiments of the present invention provide improved systems and methods for controlling urination in patients unable to voluntarily control urination, typically paralyzed patients and patients suffering from various forms of urinary incontinence. Systems according to the present invention for controlling urination comprise at least two electrodes configured to be implanted in the patient's abdomen to deliver current to the patient's pudenal nerve(s) in the form of an electrical waveform. The waveform has one or more characteristics (e.g., frequency, voltage, current etc.) configured to stimulate and/or block the patients pudenal nerve to stimulate and block the patient's pudenal nerve to cause a physiological action involved in the urination process. Such as actions may include opening of patient's urethra (which is accomplished by blocking of the pudenal nerve), contraction of the bladder or relaxation of the bladder (the latter two accomplished by stimulation of the pudenal nerve. Typically, frequency is the characteristic which is used to produce a specific physiologic action. For example, high frequencies (above 4 khz, such as in a range of 4 to 20 kHz, with a preferred value of about 5 or 6 khz) can be used to cause opening of the urethra by blocking signals from the pudenal nerve or the implanted electrodes causing it to close, while lower frequencies are used to contract the bladder (e.g., 10 to 50 hz, with a preferred value of about 20 hz), and very low frequencies are used to relax the bladder (e.g., 1 to 15, with preferred value of 5) to cease urination.

The system will also typically include an implantable sensor configured to sense information corresponding to a degree of filling of the patient's bladder. The sensor will typically being a pressure sensor configured to measure or sense pressure. Alternately, it may be a sensor adapted to measure or sense one or more of bladder wall stretch, bladder distension, or the like. Systems of the present invention may further include an implantable controller configured to deliver current to the at least two electrodes, where the delivered current is able to selectively stimulate and selectively block the pudenal nerve as will be described in more detail below. The systems may still further include an external device which is configured to receive information (e.g data such as bladder pressure or distention data) from the implantable sensor, display a value corresponding to the degree of filling of the bladder, and send signals to the implantable controller to initiate voiding of the bladder when desired by the patient or the patient's caregiver.

The systems of the present invention may optionally comprise at least a third electrode, wherein at least one of the three electrodes is configured to be implanted to deliver current to a contralateral pudenal nerve. Pudenal nerves are arranged in a bilateral fashion, and when two electrodes are employed, typically both will be connected to deliver current to one of the two sides, which may be designated as the ipsilateral pudenal nerve. When a third electrode is employed, it will typically be connected to the other pudenal nerve, which may be referred to as the contralateral pudenal nerve.

In specific embodiments, the implantable controllers are configured to selectively deliver current to the pudenal nerve in the form of a low frequency electrical waveform (e.g., in a frequency range of about 15 to 50 hz) configured to stimulate the pudenal nerve to contract the patient's bladder in order to void urine from the bladder. In order to void the urine, the patient's urinary sphincter must also be open to allow flow. Thus, the implantable controller will further be configured to deliver current to the pudenal nerve in the form of a high frequency electrical waveform (e.g., in a frequency range of about 4 to 10 khz) in order to block the pudenal nerve to open the urinary sphincter and allow the flow of urine through the urethra. Specifically the high frequency electrical waveform acts to open the urinary sphincter by blocking signals (e.g. action potentials) from the pudenal never causing the urinary sphincter to stay closed. In many embodiment the low frequency and high frequency waveforms are delivered simultaneously an initiated about the same time. However embodiments also contemplate starting the high frequency waveform first so as to open the urinary sphincter and then after a select period of time (e.g., 0.5 to 5 seconds) concurrently delivering the low frequency waveform to contract the bladder. The low and high frequency current will typically be delivered to the same ipsilateral pudenal nerve. Optionally though, the higher frequency current may also be delivered through the third electrode through the contralateral pudenal nerve in order to block the contralateral nerve. Further optionally, when it is desired to terminate urination, the patient or caregiver may initiate delivery of a current to the pudenal never in the form of a very low frequency electrical waveform (e.g., in a frequency range of about 0.5 to 15 hz) through the first or second electrode to relax the patient's bladder.

A significant advantage of the systems of the present invention is that the patient and/or the patient's caregiver will have information relating to the filling of the bladder which allows them either to initiate voiding of the bladder before the bladder is overfilled and the bladder pressure is raised to a potentially traumatic level. Also, embodiments of the invention provide information to the patient letting them know that it is time to urinate and be able to prepare for urination by providing a proper urinary receptacle or taking other preparatory steps necessary for the urination prior to actually stimulating urination via the pudenal nerve. Such information can include, for example, that on the state of fullness or filling of their bladder. The information on filling may include one or more of the distention of the bladder, the tension in the bladder wall, the pressure within the bladder or the amount of urine within the bladder. This information may include either an absolute number or a percentage of a maximum.

Conveniently, the external device initiates voiding by sending a signal to the implantable controller to deliver the low frequency current to the pudenal nerve to contract the bladder to cause the flow of urine out of the bladder and deliver the high frequency current to the pudenal nerve to open the urinary sphincter to allow urination. The external controller will often be a combination or hybrid device employing a conventional "personal digital assistant," thus described in more detail below, and an accessory appliance intended to be mated with the PDA to provide the desired communication with the implanted controller.

In a second aspect of the present invention, methods for controlling urination in a patient unable to voluntarily control urination comprise providing a control system having a visual or audible indication of bladder fullness where the control system is configured to enable the patient or caregiver to selectively stimulate the patient's pudenal nerve to initiate voiding of the bladder.

In specific aspects, the control system includes an implantable controller connected to the pudenal nerve by at least two electrodes and an external device configured to wirelessly communicate with the implantable controller. The external device provides the visual or audible signal or indication to the patient, allowing the patient to initiate voiding through an interface on the external device. Before initiating voiding, of course, the patient is able to prepare for urination by going to a toilet, providing a urinary receptacle, or the like.

Initiation of voiding is accomplished via the external device which causes the implantable controller to contract the bladder and open the patient's urinary sphincter. Optionally, the patient may simply wait until the bladder has substantially or completely voided, or may to choose to send a signal from the external device to implantable controller to relax the bladder to positively stop urination.

In a specific embodiment, the invention provides a method for controlling urination in a patient unable to voluntarily control urination, comprising providing a control system having a visual or audible indication of bladder fullness and being configured to enable the patient or caregiver to selectively stimulate the patient's pudenal nerve to initiate voiding of the bladder; determining information of bladder fullness and signaling the information to the patient; and utilizing the information to selectively stimulate the patient's prudential nerve to initiate voiding of the bladder. The information on filling may include one or more of the distention of the bladder, the tension in the bladder wall, the pressure within the bladder, the pressure/or force exerted by the bladder against an external surface, tissue or object (e.g., a sensor) the actual amount of urine within the bladder and/or a combination of one or more of all of these parameters. This information may include either an absolute number or a percentage of a maximum.

In a third aspect of the present invention, the invention provides an accessory appliance for use with a personal digital assistant (PDA) or like device which has a display, a user interface, a wireless communication capability, a rechargeable battery, and a power port for recharging the rechargeable battery (and optionally transmitting and receiving digital data) and a body for containing or holding one or more of the aforementioned components. The accessory appliance comprises a shell configured to be removably attached to the body of the PDA (or like device), where the shell includes a port which is functionally identical to the power port of the PDA. A coupling bridge within the shell is configured to connect the port on the accessory appliance with the port on the PDA when the shell is attached to the PDA body. By having the coupling bridge between the accessory appliance port and the PDA port, recharging current from a PDA cable (when attached to wall current or to a computer or other source) can be used to recharge a rechargeable battery which is part of the accessory appliance. The accessory appliance will also be able to receive and send data via the coupling bridge with both the PDA and any external computer or other device connected via the PDA power cable to the accessory appliance port. The accessory appliance may further include at least one short range wireless communication antenna configured to communicate with an implanted device and circuitry connecting the short range wireless communication antenna with the PDA.

Such accessory appliances will usually further include a microprocessor or other logic resources configured to receive data from the PDA and to process the data to provide instructions to be sent via the circuitry and the short range wireless communication antenna to the implanted device. The microprocessor of the accessory appliance can be connected to the PDA via the coupling bridge or could be connected to the PDA via a short range wireless link, such as a Bluetooth® link. In the later case, the accessory appliance will provided with an appropriate short range antenna in addition to the antenna which is provided for linking to the implanted device. It will be appreciated that transcutaneous signal transmissions required by particular radio frequency or other transmission characteristics, and a Bluetooth or other antenna on the accessory device will not be sufficient to communicate with the implanted device.

Combination of the accessory appliance and the PDA provides a number of advantages. The PDA can provide a display and user interface which can be used to communicate with the implanted device, thus eliminating the need to incorporate these features within the external device needed to control the implanted device. In addition, the PDA can further provide logical programming to help control the implanted device, reducing the need to provide processing capability within the accessory appliance itself. Usually, however, at least a minimal amount of processing capability will be provided on the accessory appliance in order to control the features and functions thereof, but the logical processing capability can optionally be shared with that provided by the PDA.

In certain embodiments, the accessory appliance will further comprise a microprocessor configured to receive data from the PDA and to process the data to provide instructions to be sent via the circuitry and the short range wireless communication antenna to the implanted device. The programmed instructions for operating the implanted device may, however, reside primarily on the microprocessor of the accessory appliance, may alternately reside on the microprocessor of the PDA, or may be shared between in the two microprocessors as is well known in the art. In still other embodiments they may reside on the Cloud and be down loaded or otherwise communicate with one or both of the aforementioned microprocessors.

In still further aspects of the accessory appliance, in addition to having a battery of the accessory appliance be recharged by the recharging capability of the PDA, the battery on the accessory appliance may further be configured to recharge the PDA battery in the event the PDA battery needs recharging. In such aspects, particular embodiments of the invention contemplate the use of battery charge monitoring software/logic programming resident on the accessory appliance microprocessor which monitor the charge (e.g. voltage and/or current) the PDA battery charge and automatically start charging the PDA battery when the PDA battery charge (e.g., voltage and/or current levels) fall below a designated threshold level.

BRIEF DESCRIPTION OF THE DRAWINGS

FIG. 1 depicts a three-channel system for stimulating pudendal nerves or branches thereof to perform one or more functions in the urination process. Pulse generator 10 is depicted as having three output channels. Wire leads 12 and 13 are attached to electrodes 14 and 15, which are placed about pudendal nerve 20. Electrode 15 is shown distal to electrode 14. In the context of a method comprising blocking the EUS and/or anal sphincter and stimulating or inhibiting contractions in the bladder and/or rectum, electrode 14 would be used to stimulate or inhibit bladder and/or rectal contractions, while electrode 15 would be used to block the EUS or anal sphincter. As needed, wire lead 16 is attached to another electrode (not shown in FIG. 1) that is placed about the pudendal nerve on the other side of the body to block the pudendal nerve on the opposite side. Pulse generator 10 is shown as implanted beneath skin 40. Output parameters of the pulse generator 10 can be controlled via a wired interface, but preferably are controlled by wireless transmission, which can be carried using any suitable wireless protocol, such as radio frequency, IEEE 802.11a/b/g, Bluetooth®, etc. Thus, in the embodiments of FIG. 1, an external controller 30 is depicted for communicating with the pulse generator 10. External controller 30 is depicted as having a display 32, such as an LCD, LED or OLED display, and a keypad 34 for entering data into the external controller 30. External controller is depicted as sending a wireless transmission 36 to pulse generator 10, though in another embodiment, data can be transferred both to the pulse generator 10 from the external communicator 30 and vice-versa, to permit monitoring of one or more parameters of pulse generator 10, including, without limitation, output signal characteristics (e.g., frequency, amplitude, etc. as outlined above) and battery strength. Activity of pulse generator 10 and external controller 30 typically is microprocessor controlled and software/firmware installed onto the pulse generator 10 and external controller 30 hardware may be used to implement the described tasks, and to provide, for example and without limitation, a GUI (graphical user interface) for the display 32, which facilitates use of the system. Both pulse generator 10 and external controller 30 may comprise any suitable electrical and electronic components to implement the activities, including, microprocessors, memory (e.g., RAM, ROM. Flash memory, etc.), connectors, batteries, power transformers, amplifiers, etc.

FIGS. 6a and 6b are lateral and cross sectional views showing an embodiment of a bipolar electrode the positioning of the electrode on the electrode cuff placed over a branch of the pudenal nerve.

FIGS. 7a and 7b are lateral and cross sectional views showing an embodiment of a tripolar electrode the positioning of the electrode on the electrode cuff placed over a branch of the pudenal nerve.

DETAILED DESCRIPTION OF THE INVENTION

Embodiments of the invention provide devices, systems and methods for delivering stimulating signals to paralyzed and other patients incapable of voluntary control of urinary function. Many embodiments provide the stimulating signals to these patients in the form of electrical currents so as to so as to initiate and/or control their urinary function. In particular embodiments, systems of the present invention provide both an external device and an implanted device which are capable of working in combination to allow a patient to selectively control urinary function by stimulating the pudenal nerve to initiate urination and optionally to terminate urination. Also in particular embodiments, the present invention provides real time information relating to the patient's bladder fullness, usually by measuring and indicating pressure but optionally, by measuring and indicating bladder distension or stretching of the bladder wall.

The system components for initiating and optionally terminating urination may be generally the same as those described in the systems of U.S. patent publication 2014/0249595, which has previously been incorporated herein by reference herein for all purposes. The systems of that patent publication, however, provide no means for giving a patient feedback or information relating to bladder fullness, making it more difficult for the patient to determine when to urinate. Moreover, the systems of that patent publication rely on dedicated external controllers where all system components are dedicated and intended for use only in controlling the disclosed systems.

Figure 1:
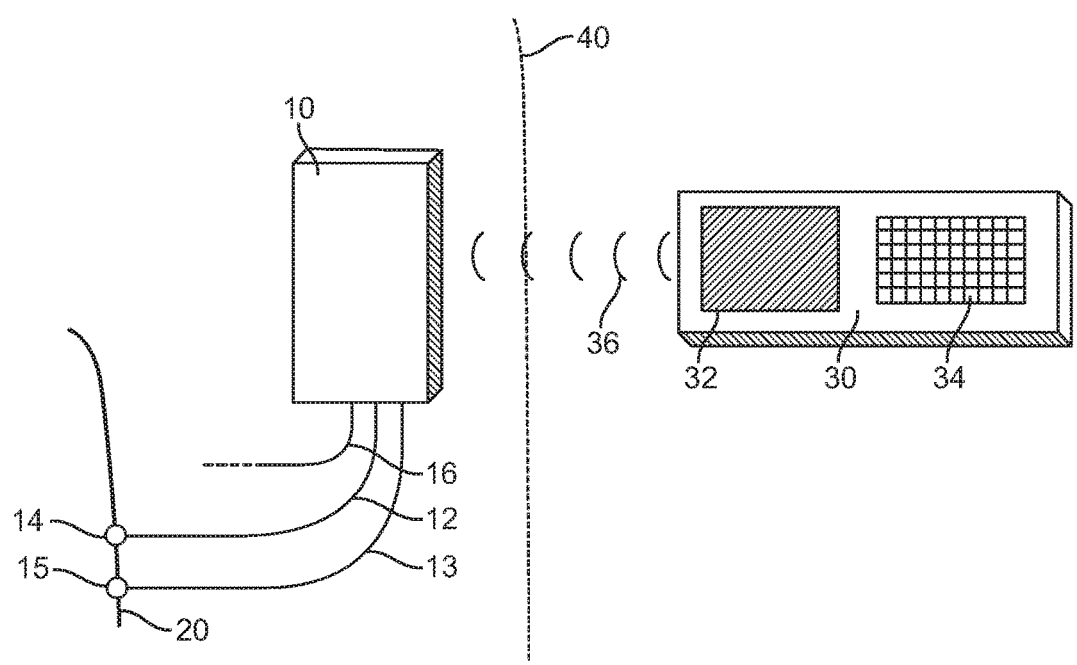
FIG. 1 illustrates a prior art system for selectively stimulating the pudenal nerves to control urination taken from US Patent Publication No. 2014/0249595, the full disclosure of which has previously been incorporated herein by reference. In particular.
Figure 2:
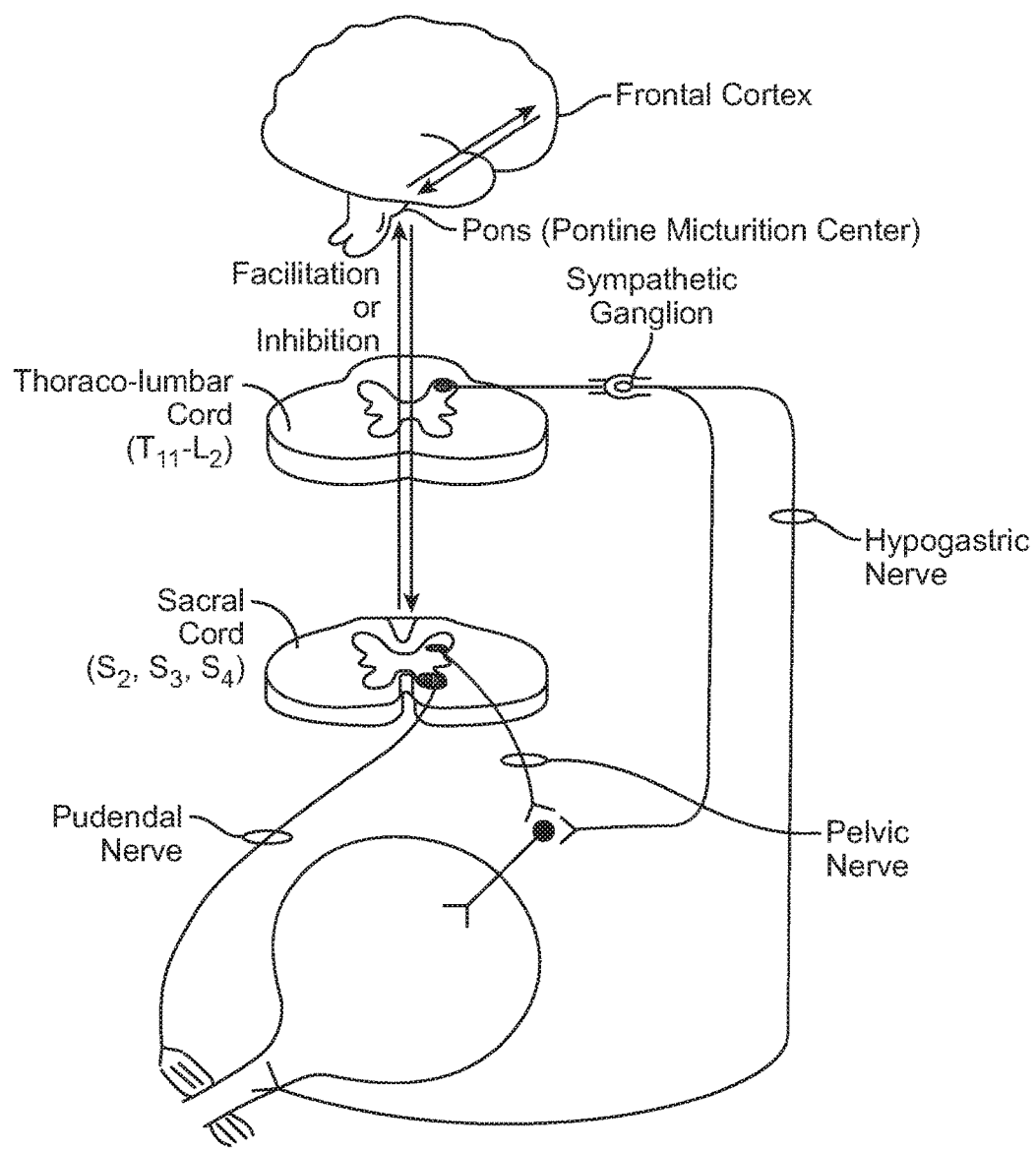
FIG. 2 is a schematic illustration showing normal innervation of the urinary tract.

As many embodiments of the invention relate to approaches for controlling urinary function, particular for patients who are paralyzed and/or who are otherwise incapable of voluntary control of urinary function a brief explanation will now be presented of the neural circuitry for control of the urinary function and what happens as result of spinal cord injury. Referring now to FIG. 2, the neural circuitry that controls the urine voiding process is complex and highly distributed: it involves pathways at many levels of the brain, the spinal cord and peripheral nervous system and is mediated by multiple neurotransmitters. The two goals of normal bladder function are to store urine until there is a socially acceptable time and place and to empty the bladder in a coordinated fashion. The act of voiding is primarily controlled by the parasympathetic nervous system, primarily via the pelvic nerve (S2-S4); whereas, storage is primarily accomplished via the sympathetic nervous system (specifically at T10-L2, hypogastric nerve) which increases urethral closure pressure and inhibits parasympathetic nerves to the bladder as shown in FIG. 2. When the path between the sacral micturition center and the brain is intact, voiding is coordinated and occurs by relaxation of the striated (external) urethral sphincter, contraction of the detrusor, and opening of the bladder neck and urethra. When the path between the brain and the sacral micturition center is damaged or disrupted (e.g., by spinal cord injury) the coordination between detrusor and sphincter during voiding is impaired in a condition known as Detrusor-sphincter dyssynergia or DSD. DSD is commonly characterized by involuntary contractions of the external urethral sphincter during an involuntary detrusor contraction. Sequelae of DSD include hydronephoris, recurrent pyelonephritis, and renal failure. DSD is caused by neurological lesions between the brainstem and the sacral spinal cord and specific causes of DSD include: traumatic spinal cord injury, multiple sclerosis, spinal dysraphism, and transverse myelitis.

Figure 3:
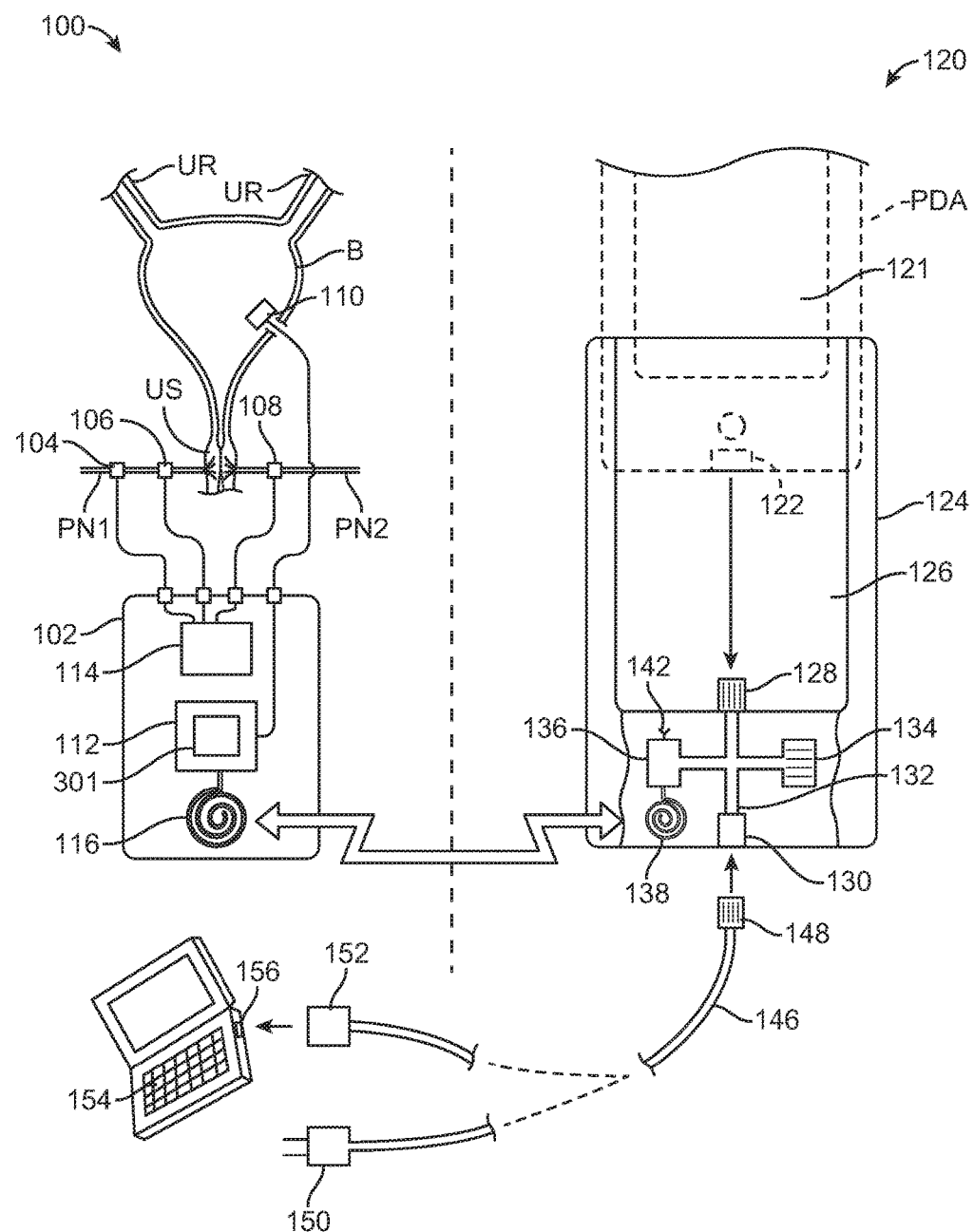
FIG. 3 is a schematic illustration showing the system components of the present invention including the implanted components, the components of the external device and the optional connections to a power source and to a computer or other programming source.

Referring now to FIG. 3, a system 100 constructed in accordance with the principles of the present invention typically comprises both an implantable controller 102 and an external controller 120. Though in some embodiments, it may only include an implantable or external controller. The implantable controller 102, will be of the type intended for long-term implantation and will have at least first and second electrodes 104 and 106 intended for connection to at least one branch of the pudenal nerves PN1 and PN2. Typically, electrodes 104 and 106 are configured for connected to the same pudenal nerve PN1. Optionally, a third electrode 108 will be provided, typically for connection to a contralateral branch of the pudenal nerves PN2. According to one or more embodiments, third electrode 108 can be configured to be used by controller 120 to deliver a current to stop or otherwise inhibit bladder contraction so as to stop urination. It may also be used as to block the pudenal nerve to open or keep open the urinary sphincter.

Of particular interest to the present invention, the system 100 will typically further include a bladder fullness sensor 110, which may correspond any one or more of those sensors described earlier, including for example, pressure sensors, bladder distension sensors, bladder wall stretch sensors, and the like. One or more of these sensors may correspond to strain gauges includes MEMs based strain gauges known in the art. According to various embodiments sensor 110 can be positioned on or adjacent the bladder wall. Further the sensor may have an atraumatic biocompatible coating or layer (e.g., silicone or polyurethane) configured to minimize irritation of the bladder wall including that causing any type of wound healing response (e.g. collagen or cellular deposition or the like) so as to minimize any changes to the mechanical properties to the section of the bladder wall to which the sensor is attached. This may also be accomplished through the size and shape of the sensor 110. Desirably, sensor 110 has a rounded shape so as to minimize any stress applied to the wall on its edges and also has a stiffness less than equal to the bladder in various states of distention. The purpose of these sensors will be to sense information corresponding to a degree of bladder fullness to determine when the bladder has reached a threshold level of fullness as it is filled through the ureters UR from the kidneys (not shown). In various embodiments, the information collected by sensors 110 can calibrated against the patient themselves by taking another measurement of bladder pressure during a set amount of bladder filling using a foley catheter or other like device and bladder pressure measurement method known in the art. As discussed earlier, overfilling of the bladder can back urine into the kidneys through the ureters presenting substantial risk of morbidity and mortality to the patient. Thus in use, embodiments of the invention employing sensors 110 can reduce the risk of back flow of urine into the kidneys and the associated risk of morbidity and mortality to the patient including that caused by kidney damage.

The implantable controller 102 will include a microprocessor 112 for managing the functions of the controller, including controlling a stimulator or pulse generator 114 to deliver stimulation energy to the electrodes 104, 106, and optionally 108. The microprocessor 112 will further be connected to an antenna 116 which provides transmission capability to the implantable controller for wirelessly communicating with the external controller 120. Usually, the antenna 116 will be designed to operate at a radio frequency (RF) suitable for transcutaneous communication. In particular embodiments, the antenna can be configured to operate in the MICS frequency range known in the art. Optionally, the antenna 116 may further be configured to receive energy from a suitable RF source to be stored in an on-board battery (not shown) or other energy storage means known in the art (e.g., a capacitor or super capacitor) in a conventional manner. Alternatively, the implantable controller may be configured to run on non-rechargeable batteries requiring periodic battery replacement. In various embodiments, antenna 116 may be a tuned or tunable antenna, may have a variety of shapes such as the coiled shaped as shown in FIG. 3 as well as straight, square, rectangular or other like shape, with the length or other dimension selected for transmission at particular frequency or range of frequencies. Further in particular embodiments, antenna 116 or other antenna described herein may be a stub antenna and/or a stub tuned antenna.

The external controller 120 may be a relatively simple controller of the type described in US Patent Publication No.

2014/0249595, modified only to receive bladder fullness data from the implanted controller and to display such data on the display screen of that external device. Preferably, however, the external controllers on the present invention will be a combination or assembly including both a shell component 124 and a conventional personal digital assistant (PDA) of a type commonly available. As used herein, reference to a personal digital assistant (PDA) will mean any small, mobile, usually hand-held device that is able to provide computing and storage information and retrieval capabilities. The PDA's use in the present invention will include at least a body, display, a user interface, wireless communication capability, a rechargeable battery, and a power port for recharging the rechargeable battery, and usually for also transmitting data to and from other external devices, such as computers, tablets, cell phones and the like. The wireless communication capability can be in the form of an RF communication device e.g. an RF communication chip configured to communication in a BLUETOOTH or other related format. Exemplary PDA's at the present time include "smart phones," of the type sold by Apple Computer, Samsung, and others. In the future, such smart phones may further evolve and may be identified by different names, but it is expected that they still will be compatible with the external control components of the present invention.

Referring again specifically to FIG. 3, the shell 124 has a receptacle region 126 which can slidingly receive the PDA so that a power/data port 122 on the PDA is able to mate or otherwise engage with a power/data plug 128 on the shell at the bottom of the receptacle region 126. In alternative embodiments, receptacle region 126 can be configured to receive the PDA by means of a snap or press fit over the PDA or by a joining means such as use of VELCRO or a releasable adhesive. In these and other embodiments, the receptacle region 126 is aligned and otherwise configured such that, when the PDA is fully inserted, the plug 128 will be fully inserted into the port 122. In use, such embodiments allows for a complete electrical and data connection between the PDA and the accessory device without the user having to manipulate plug 128 or the receptacle region 126. Further as described above, this can be achieved by the sliding movement alone of the PDA into the receptacle region 126 and/or by the action of snapping or pressing the PDA into the receptacle region 126 and/or pressing the receptacle region over the PDA. Such alignment for plug 128 can be achieved by control of the tolerances of the receptacle region 126 and/or plug 128, and/or the use of guiding structures or other guiding means (not shown) on the receptacle region and/or receptacle region 126 and/or plug 128. It will be appreciated that the plug 128 will typically be identical to the plug which is provided by the vendor of the PDA and intended for recharging the PDA and/or exchanging data with the PDA and the computer, tablet, or other external device. However, in other embodiments, plug 128 may not necessarily be the same as the plug on the PDA and may be configured to attach to an adaptor to connect to the plug on the PDA. In various embodiments, plug 128 may correspond to any of the USB connectors known in the art including, for example, USB A, USB B, USB Micro A, USB Micro B, USB Mini A and USB Mini B. In particular preferred embodiments, plug 128 may correspond to a USB Type C connector including for example a USB 3.1 Type C connector. In use, use of a USB type C or other like connectors for plug 128 including USB 3.1 allows for one or more of the following: i) easier connection and faster data transmission (e.g., up to about 10 Gbps.) between logic units 136 and one or more controllers associated with the PDA, like device or external computer; ii) faster and more complete charging of battery 134 (including an input power of up to 100 watts at 20 Volts); and iii) compatibility with a greater number of PDA's, like devices or an external computer.

According to one or more embodiments of shell 126, plug 128 will be connected to a further port 130 at the bottom of the shell by a coupling bridge 132. At a minimum, the coupling bridge will provide electrical connections so that when a vendor-supplied plug 148 on cable 126 (intended to be plugged directly into port 128 on the PDA) is plugged into the port 130, the PDA will see all connections as if the plug 148 were plugged directly into the port 128. In addition, the coupling bridge 132 will provide a number of capabilities to the circuitry within the shell 124. At a minimum, the coupling bridge 132 will be connected to a rechargeable battery 134 which is part of the shell so that the rechargeable battery 134 will be maintained fully charged so long as the PDA is being used and is plugged in via the port 130.

In many embodiments, the coupling bridge 132 will usually be connected to provide a data link to a processor or other logic unit 136 which is part of the shell 124 and which controls communication of the shell with the implantable controller 102. Logic unit 136 may also correspond to one or more of an Application Specific Integrated Circuit (ASIC), state device/machine, analogue device or other logic means known in the art. The processor or logic unit 136 will be connected (directly or operably) with an antenna 138 which is specifically configured to communicate with the antenna 116 which is part of the implantable controller 102. Usually, both antennas 116 and 138 will be configured for radio frequency transmission at a range selected to operate transcutaneously. Commonly, the antennas are coil-like devices, but other antenna configurations may be provided (e.g. a stub antenna). Optionally, the antenna and logic unit 136 may include a further antenna 142 intended for digital communication with the PDA and/or other external digital devices. Data communication between the PDA and the processor logic unit 136 may thus be effected via the coupling bridge 132, via the digital antenna 142 or both. Typically digital antenna 142 is an RF based antenna configured for Blue Tooth communication with the PDS, however it may configured for other frequency ranges outside the Blue Tooth protocol may also be used. For example, in particular embodiments, one or more of antennas 116, 138, 142 and logic unit 136 may be configured to communicate within the Medical Implant Communication Service (MICS) frequency band, typically between 402 and 405 MHz, though other frequencies are also considered.

Once the PDA is fully inserted into the shell 124, the combination of the PDA and the shell will be configured to be used as a single unit with the patient and/or caregiver entering commands and data using the PDA interface, typically touch screen 121, and data being shown on the same display 121. Optionally, data may be entered by speech recognition means on the PDA and alarms and other signals may be provided by an audio capability of the PDA.

In normal operation, the implantable controller 102 will be continuously or periodically monitoring bladder fullness using the sensor 110 and information regarding bladder fullness (e.g. an amount of bladder stretching or distension (absolute or percentage), an amount of bladder fullness (absolute or percentage) or bladder pressure) will continuously or periodically be transmitted via the microprocessor 112 and antenna 116 to the PDA via antenna 138 and the processing logic unit 136.

In some cases, it will be desired only to recharge the PDA and battery 134 of the shell 124 where the cable 146 may be plugged into the wall through a power supply 150. Alternatively, when it is desired to reprogram the PDA, the unit may be plugged into a personal computer 154 via a USB plug 152 which goes into the USB port 156 on the computer.

Figure 4:
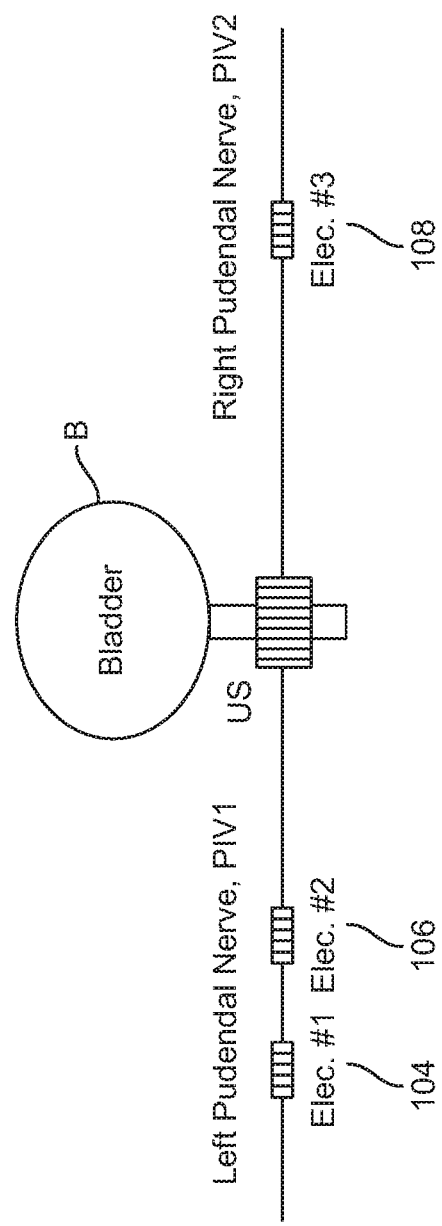
FIG. 4 is a schematic illustration showing an embodiment of positioning of the implantable electrodes on the left and right Pudenal nerve.

Referring now to FIG. 4, in specific embodiment electrodes 104, 106 are connected to the left pudenal nerve and electrode 108 to the right pudenal nerve. Electrode 104 can be used to send very low frequency electrical waveforms (typically g. 1 to 10 hz) to stimulate the pudenal nerve to keep the bladder relaxed or a low frequency wave forms to open the bladder (e.g. 10 to 50 hz). Electrode 108 is used to send high frequency waveforms (e.g. 4 to 20 kHz) to block the right pudenal nerve (typically from natural nerve impulses) to open or keep the urinary sphincter EUS. Electrode 106 is also used to send a high frequency signal to block the left pudenal nerve (e.g., from waveforms from electrode 104) so as to open or keep open the urinary sphincter.

Figure 5A:
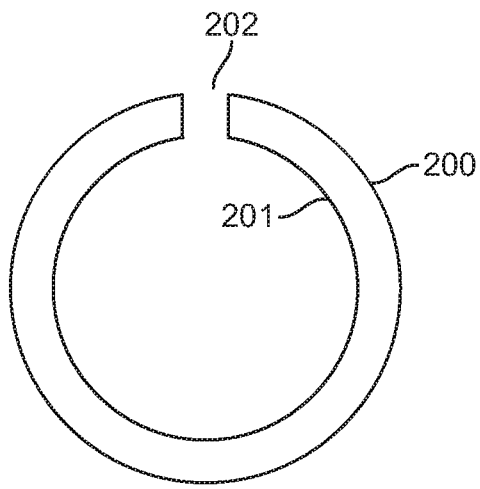
FIGS. 5a and 5b are lateral view showing an embodiment of a cuff configured to be placed over a branch of the pudenal nerve (FIG. 5a); and placement of the cuff over a branch of the pudenal nerve (FIG. 5b)
Figure 5B:
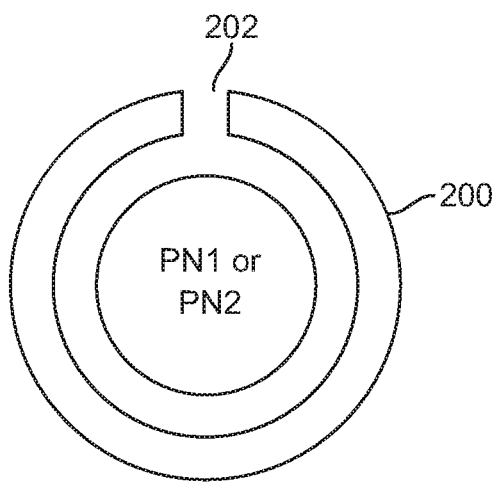

Referring now to FIGS. 5-7 in various embodiments one more of electrodes 104, 106 and 108 can be positioned on a cuff 200 configured to fit over and remain on branch of the pudenal nerve. The electrodes 104, 106 and 108 can be positioned so as to have a radial or axial orientation in relation to the cuff 200. The cuff 200 will usually have a circumferential opening 202 to allow to cuff to be fit over the pudenal nerve by the doctor. Cuff 200 is desirably fabricated from elastic materials such as silicone or urethane and has sufficient radial spring force to clamp down on and remain on the pudenal nerve once so placed. At the same time the dimensions and mechanical and material properties of the cuff are such that it desirably exerts not more than about 150 mm of pressure on the pudenal nerve or about 0.5 Newtons of force as forces below this amount serve to maintain the health of the pudenal nerve. Also the cuff 200, including its inner surface 201 are desirably constructed from atraumatic biomaterials such as one or more of silicone, polyurethane, TEFLON, and the like so as to be atraumatic to the pudenal nerve including the pudenal nerve sheath. The inner surface of cuff 200 may include one more drug eluting coatings known in the art to improve the biocompability of the coating and reducing any inflammation or tissue adherence at the interface of the cuff with the pudenal nerve. Desirably cuff 200 is also constructed from insulative materials so as to prevent the leaking of any current outside of the cuff and thus prevent unwanted stimulation or block of another portion of branch of the pudenal nerve.

Figure 6B:
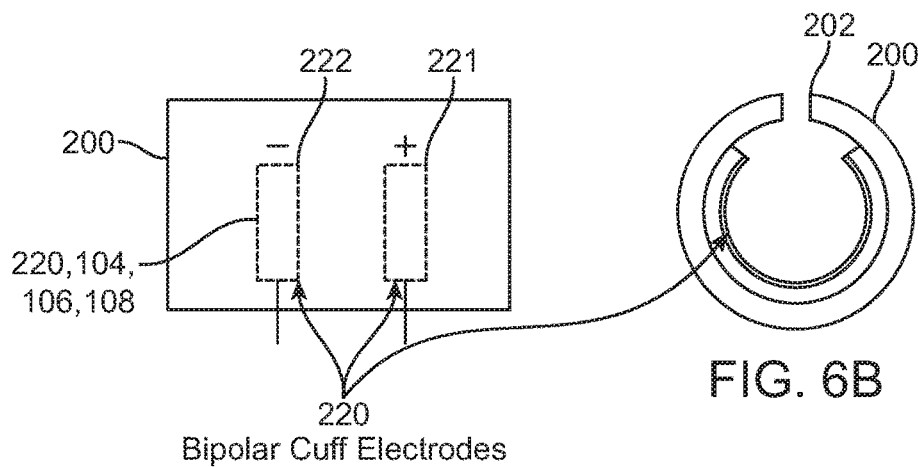
Figure 7B:
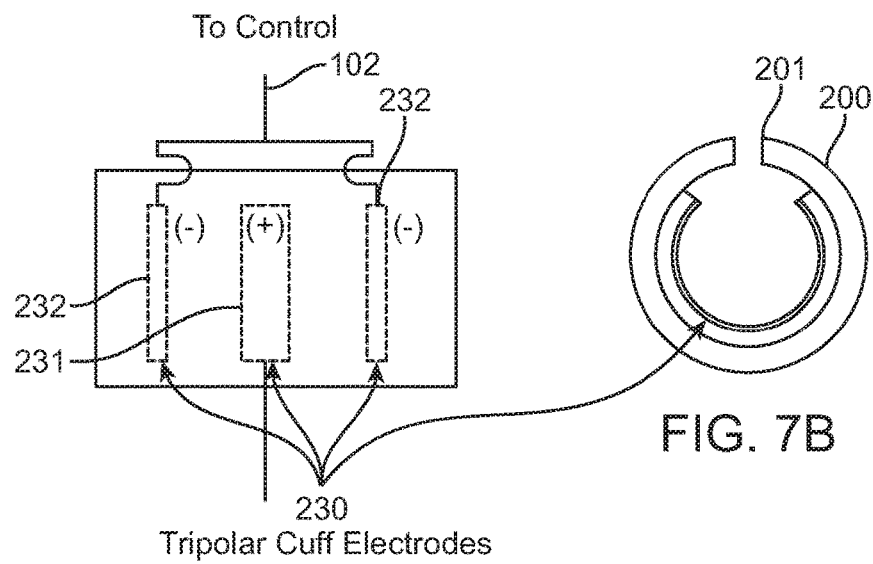

Referring now to FIGS. 6a and 6b in various embodiments one more of electrodes 104, 106 and 108 can be figured as bi-polar electrodes 220 having a positive and negative pole or portion 221 and 222 which may be positioned radially or axially around cuff 200. Referring to now to FIGS. 7a and 7b, in still other embodiment one or more of electrodes 104, 106 and 108 can be configured as tri-polar electrodes 230 having a positive pole or portion 231 and negative portions 232. In use embodiments of such a tripolar electrodes 230 serve to reduce the leakage of any current outside of cuff 200 and in turn reduce unwanted stimulation or blockage of a given branch of the pudenal nerve or a surrounding branch.

Figure 8:
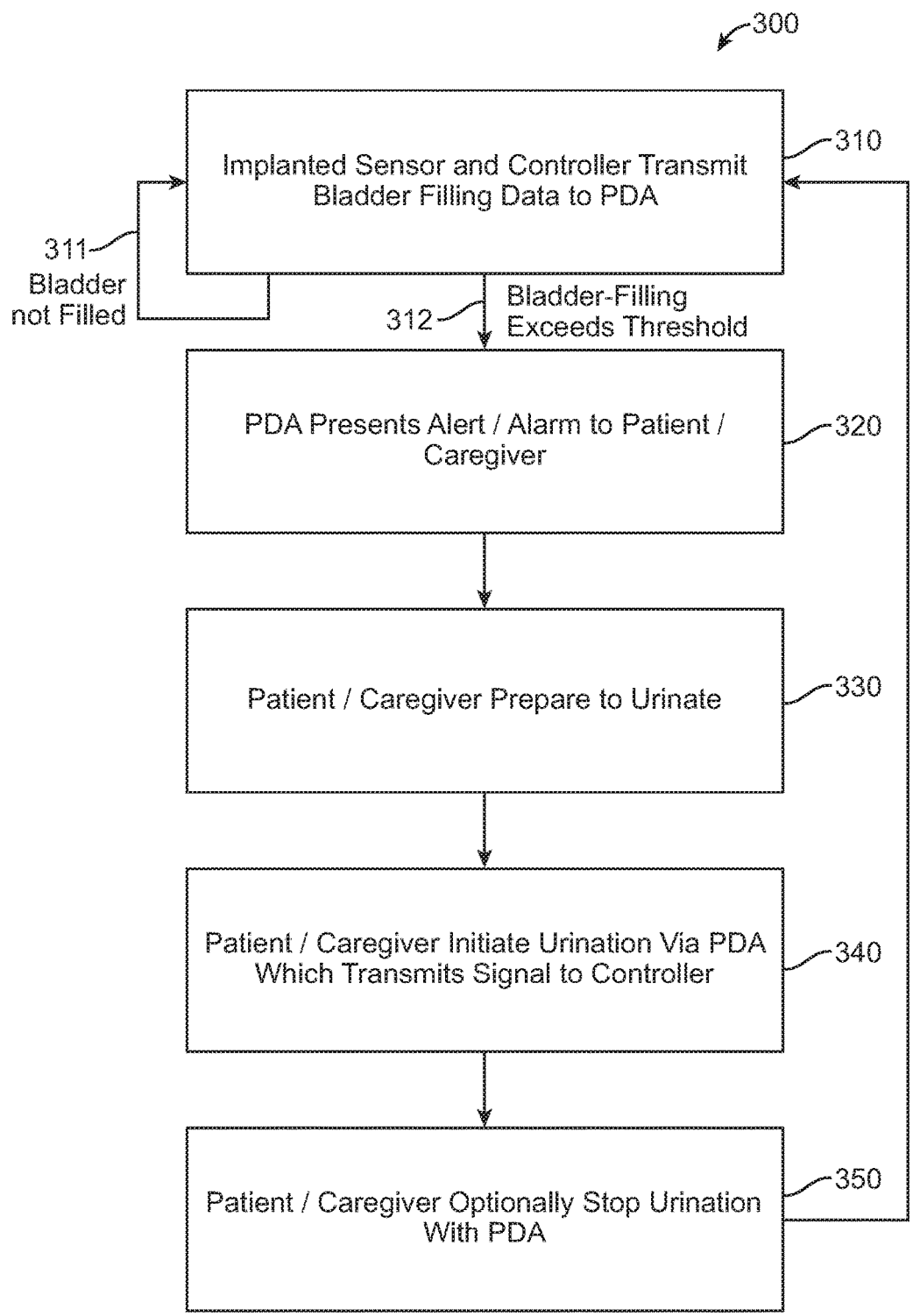
FIG. 8 is a block diagram illustrating certain method steps according to the present invention.

Referring now to FIG. 8, an embodiment of a method for utilizing an embodiment of system 100 to control urination along with an algorithm 300 for doing so will now be illustrated. Algorithm 300 may be implemented by an electronic instruction set (which may be in the form of a software module 301) resident on microprocessor 112 or other logic resources contained in controller 102 and/or on logic unit 136 or other logic resources on PDA/controller 120. In a first step 310, the implanted sensor and controller to transmit bladder filling/information (e.g. in the form of bladder pressure, wall distention or wall stretch data), either continuously or periodically to the PDA or a combination of both. So long as the bladder is not filled (event 311), the PDA can display that status or can simply display nothing. In the event that the signal indicating bladder filling exceeds a threshold level (event 312); however, the PDA will present an alert or alarm to the patient or caregiver in step 320. The alarm may be a visual one displayed in various graphic forms on the display screen. Alternatively, the alarm may be audible via a small speaker on the PDA, or in some cases the alarm or alert may be both visual and audible. After receiving the alert or alarm, the patient or caregiver knows that the bladder should be emptied (e.g. by urination) in order to prevent over pressure of the bladder and potential damage to the kidneys. The patient or caregiver then has time to go to a lavatory or obtain the appropriate receptacles to collect the urine during urination. After appropriate preparation step 330, the caregiver can use the PDA to signal the implanted controller to provide appropriate signals to the pudenal nerves in order to initiate urination in step 340. Useful stimulation frequencies, currents and voltages for achieving a selected result are presented below in Table 1. In specific embodiments the current can range from about 0.1 to 14.9 mA, with a preferred embodiments of about 1 to 14 ma and more preferably in range of about 1 to 1 mA. It should be appreciated that embodiments of the invention are not limited to these value, but rather other values are considered as well. It should also be appreciated that for these and other values and parameters cited herein, the term "about" means within +/−10% of a stated value for a dimension, characteristic, physical property and the like.

TABLE 1

Bladder Stimulation Parameters

| Stimulation Frequency | Current, Voltage | Stimulation Site | Result |
| --- | --- | --- | --- |
| 0.5 to 15 Hz; preferred, 1 to 10 Hz, preferred value of 5 Hz | <15 mA; 50 V | Pudenal Nerve | Relax Bladder |
| 10 to 50 Hz; preferred 20 Hz | <15 mA; 50 V | Pudenal Nerve | Contract Bladder |
| Above 4 kHz, 4 to 30 kHz, preferred 4 to 20 kHz, more preferred 4 to 10 kHz, preferred value of about 6 kHz | <15 mA; 50 V | Contralateral Pudenal nerve | Inhibit Contraction of Urinary Sphincter to open sphincter |

According to one embodiment, urination can be allowed to terminate as a result of complete voiding of the bladder and the stimulatory signals can be terminated at that time. Alternately, the PDA and an implanted controller may be utilized to send a signal in step 340 to relax the bladder which will terminate urination even if the bladder is not completely voided. After urination is terminated, the patient and caregivers may continue with other activities and rely on the systems of the present invention to again alert them when bladder filling has exceeded the allowable threshold level. In various embodiments, delays can be built into the system between the time the patent signals for voiding and the voiding waveform is sent as well as between the time between when the waveform is sent to stop voiding after the patient signals it (e.g., using the PDA). The delays can be in the tenths of seconds or longer.

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the device can be sized and otherwise adapted for various pediatric and neonatal applications as well as various veterinary applications. They may also be adapted for the urinary tracts of both male and females. Further, those skilled in the art will recognize, or be able to ascertain using no more than routine experimentation, numerous equivalents to the specific devices and methods described herein. Such equivalents are considered to be within the scope of the present invention and are covered by the appended claims below.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. An accessory appliance for use with a personal digital assistant (PDA) having a body, a display, a user interface, wireless communication capability, a rechargeable battery and a power port, said accessory appliance comprising:
   a shell configured to be removably attached to the body of the PDA;
   a port functionally identical to the power port of the PDA;
   a coupling bridge configured to connect the port on the accessory appliance with the port on the PDA when the shell is attached to the PDA body;
   a rechargeable battery connected to receive recharging current from the coupling bridge;
   at least one short range wireless communication capability configured to communicate with an implanted device; and
   circuitry connecting the short range wireless communication capability of the accessory appliance with the PDA.

2. The accessory appliance of claim 1, further comprising a microprocessor configured to receive data from the PDA and to process the data to provide instructions to be sent via the circuitry and the short range wireless communication capability to the implanted device.

3. The accessory appliance as in claim 1, wherein the program for operating the implanted device resides at least primarily on the microprocessor on the accessory appliance.

4. The accessory appliance as in claim 1, wherein the microprocessor is programmed to operate with other programming residing substantially on the PDA and/or the implanted device.

5. The accessory appliance of claim 1, wherein the rechargeable battery of the accessory appliance is connected to selectively provide recharging current to the rechargeable battery of the PDA through the coupling bridge.

6. The accessory appliance of claim 1, further comprising a second short range communication capability configured to communicate with a short range wireless communication capability on the PDA.

7. The accessory appliance of claim 1, wherein the coupling bridge is configured to allow data exchange between the PDA and the circuitry of the accessory appliance.

8. The accessory appliance of claim 1, wherein the shell comprises an exterior case configured to cover a back side of the PDA.

9. The accessory appliance of claim 1, wherein the shell is configured to be slidably attached to the shell of the PDA.

10. The accessory appliance of claim 1, wherein the bridge is configured to align the port on the accessory appliance with the port on the PDA when the shell is attached to the PDA body.

* * * * *